United States Patent [19]

Eoga et al.

[11] Patent Number: 5,476,607
[45] Date of Patent: *Dec. 19, 1995

[54] PERBORATE:PERSULFATE:PROTEASE DENTURE CLEANSER POWDER COMPOSITION

[75] Inventors: Anthony B. Eoga, Boonton; Richard G. Moran, Lake Hopatcong, both of N.J.

[73] Assignee: Warner-Lambert Company, Morris Plains, N.J.

[*] Notice: The term of this patent shall not extend beyond the expiration date of Pat. No. 5,384,062.

[21] Appl. No.: 348,020

[22] Filed: Dec. 1, 1994

Related U.S. Application Data

[63] Continuation-in-part of Ser. No. 160,378, Dec. 1, 1993, Pat. No. 5,384,062.

[51] Int. Cl.$^6$ .............................. A61K 7/30; C11D 3/39; C11D 3/48; C11D 17/00
[52] U.S. Cl. .............................. 252/99; 252/95; 252/102; 252/106; 252/174; 252/174.12; 252/174.23; 252/527; 252/DIG. 2; 252/DIG. 11; 252/DIG. 12; 252/DIG. 16
[58] Field of Search .............................. 252/95, 99, 102, 252/106, 174, 174.12, 174.23, 527, DIG. 2, DIG. 11, DIG. 12, DIG. 16

[56] References Cited

U.S. PATENT DOCUMENTS

| 4,155,868 | 5/1979 | Kaplan et al. | 252/95 |
| 5,384,062 | 1/1995 | Eoga et al. | 252/99 |

FOREIGN PATENT DOCUMENTS

| 253772 | 1/1988 | European Pat. Off. | A61K 7/30 |
| 9210165 | 6/1992 | WIPO . | |

*Primary Examiner*—Paul Lieberman
*Assistant Examiner*—Alexander G. Ghyka
*Attorney, Agent, or Firm*—Michael J. Atkins

[57] ABSTRACT

An anhydrous denture cleansing effervescent powder is disclosed comprising anhydrous perborate, a perborate monohydrate, a lubricant and compression aid, a monopersulfate, one or proteolytic enzymes, a sequestering agent, and, optionally, excipients, builders, colors, flavors, and surfactants.

34 Claims, No Drawings

PERBORATE:PERSULFATE:PROTEASE DENTURE CLEANSER POWDER COMPOSITION

CROSS-REFERENCE TO RELATED APPLICATIONS

This is a continuation-in-part of application Ser. No. 08/160,378, filed on Dec. 1, 1993 now U.S. Pat. No. 5,384,062.

BACKGROUND OF THE INVENTION

1. Field of the Invention

The invention relates to a denture cleansing powder composition and a process for making such a composition.

2. Description of the Related Art

Denture cleansing generally is carried out either by brushing dentures with a paste or by soaking dentures overnight in an aqueous cleansing solution. Aqueous denture cleanser solutions are known and generally comprise tablets, granules, or powders that are dissolved in water to form a cleansing bath or cleansing system in water.

One type of denture cleansing composition uses an effervescent system including sodium bicarbonate, citric acid and/or alkaline proteolytic cleaning enzymes, bleaching or oxidizing agents, such as alkali metal and alkaline earth metal, perborates, e.g. anhydrous sodium perborate and sodium perborate monohydrate (herein "perborates"), and monopersulfates. A second type of denture cleansing composition uses cleaning enzymes and anhydrous sodium perborate in combination with sodium perborate monohydrate. There are no persulfates in this second type of composition.

The cleansing systems produced by both of these compositions when dissolved in water have drawbacks. The pH of the aqueous solution in the first system is too low (i.e. too acidic) for fully effective cleaning enzyme activity. In addition, the reaction of the monopersulfate in the composition with chlorides in the water produces a hypochlorite which inactivates the cleaning enzymes in the composition, further depressing their efficacy. The hypochlorite also reacts with expensive fragrances in the composition, depressing their efficacy.

The use in compositions of perborate monohydrates that do not inactivate proteolytic cleaning enzymes either directly or indirectly is known. However, the use of potassium monopersulfate in the form of "OXONE", in the presence of perborate monohydrate, in a weight ratio of approximately 3:1 has been shown to result in the formation of a sufficient amount of hypochlorite in water to deactivate alkaline proteolytic cleaning enzymes. U.S. Pat. No. 5,118,623 to George Boguslawski and John W. Shultz of Solvay Enzyme Inc., issued Jun. 2, 1992, discloses that many cleaning enzymes are inactivated in the presence of chlorine and other halogens. A paper by Waku et al, CA 78(17):107533p discloses inactivy of enzymes in the presence of as little as 0.2 pans per million free chlorine.

The pH of the aqueous solution in the second system is too high (i.e. too basic). This high pH has a tendency to destroy the fragrance of the cleaning solution. In addition, the pH of the second type of composition may be too high for optimal activity of the cleaning enzyme.

There have been efforts, with limited success, to develop compositions in which deactivation of cleaning enzymes and fragrances do not occur, while good denture cleaning efficacy is still provided.

U.S. Pat. No. 4,409,118 to Anthony Eoga, issued Oct. 11, 1983, discloses an effervescent cleansing composition in tablet form comprising: (1) a phosphate salt; (2) a silicate salt; and (3) at least one perborate salt. At least part of the perborate salt is in a compacted granulated mixture with a polymeric fluorocarbon.

U.S. Pat. No. 4,857,224, to Anthony Eoga, issued Aug. 15, 1989, discloses an effervescent cleansing composition in tablet form comprising: (1) a pregranulated and compressed mixture of an anhydrous perborate, a perborate monohydrate and a polymeric fluorocarbon compound, and (2) a monopersulfate compound. This composition is useful for forming a composition from monopersulfates and anhydrous perborates.

SUMMARY OF THE INVENTION

One object of the invention is to provide a denture cleansing powder with reduced hypochlorite formation, thereby eliminating the problem of deactivation of alkaline proteolytic cleaning enzymes.

A further object of the invention is to provide a denture cleansing powder capable of dissolving in an aliquot of water to produce a denture cleansing bath having a pH suitable for alkaline proteolytic enzymatic cleaning of dentures.

A further object of the invention is to provide a denture cleansing powder that provides a burst of fragrance upon dissolution of the effervescent 2powder in water, and retains a substantial amount of fragrance when the resultant solution is allowed to stand overnight.

A further object of the invention is to provide a denture cleansing powder capable of removing non-stained plaque, stained plaque, non-stained tartar, stained tartar, and any residue or aftertaste which appears to result from a combination of plaque, stained plaque, tartar and stained tartar.

Additional objects and advantages of the invention will be set forth in part in the description that follows. The objects and advantages of the invention may be realized and attained by means of the examples and combinations described in detail herein and in the appended claims.

These and other objectives are achieved by the present invention, which relates to new denture cleansing compositions and their method of preparation comprising:

(a) a pregranulated compressed mixture of an anhydrous perborate, a perborate monohydrate and a lubricant and compression aid; and (b) a monopersulfate compound;

(c) non-granulated perborate monohydrate;

(d) an effective amount of a proteolytic cleaning enzyme to disrupt the proteinaceous material in plaque;

(e) an effective amount of sequestering agent such as ethylene diamine tetracetic acid (herein "EDTA") to remove calcium deposits and calculus (also referred to herein-as "tartar" deposits). The relative amounts of proteolytic enzyme and sequestering agent is sufficient to be effective to remove stains from both plaque and calculus deposits; and (f) An effervescence-producing composition, wherein the concomitant disruption of proteinaceous material and the sequestering of calcium and calculus deposits results in the removal of calculus and plaque deposits as well as the removal of stained calculus and stained plaque deposits.

DETAILED DESCRIPTION OF THE INVENTION

The present invention relates to improved denture cleansing compositions containing EDTA, anhydrous perborate, perborate monohydrate, polymeric fluorocarbon, and proteolytic cleaning enzymes that has excellent cleaning properties. The invention also provides a denture cleansing powder that provides a burst of fragrance when dissolved in solution, and that provides for an enhanced fragrance retention in solution overnight. The invention also provides a powder for efficient cleaning of the dentures by brushing. The invention further provides for the removal of residue from dentures after simple rinsing of the dentures under warm water.

The inventive composition is unique in solving some of the fragrance and cleaning problems associated with the inclusion of enzymes in denture cleansing compositions. The new inventive composition provides cleaning efficacy and fast dissolution as required of powder cleansers. In addition, the components of this denture cleanser react less with the fragrance additives than the components of other denture cleansers. Therefore, less fragrance additives are needed to produce the desired fragrance effect, thereby lowering cost. Additionally, the powders formed from these new compositions exhibit a strong fragrance. The solution formed from the powders provides an initial burst of fragrance, and the solution retains a substantial amount of fragrance when used for soaking dentures overnight. The anhydrous perborate is preferably an alkali metal perborate or an alkaline earth metal perborate. The amount of anhydrous perborate in the composition can be between about 5% and 25% by weight of the composition. The amount of perborate monohydrate in the composition can be between about 30% to about 45% by weight of the composition.

The weight ratio of anhydrous perborate to perborate monohydrate in the composition is from about 1:3 to about 1:1. The preferred perborate monohydrate is a non-compacted sodium perborate monohydrate in the form of a predried product containing about 0.3% to about 1.5% by weight of water, and preferably less than about 0.2% to about 0.3% by weight of water.

The invention also comprises lubricant and compression aids. Lubricant and compression aids insure good release of the composition from the composition die and are well known in the art. Sodium lauryl sulfate, sodium benzoate, polyethylene glycol, talc, metal stearates and polymeric fluorocarbons are all known and acceptable lubricant and compression aid. Although it is insoluble, polytetrafluoroethylene (herein "PTFE") is the preferred lubricant and compression aid. The lubricant and compression aid comprises from about 0.1 to about 0.8% by weight of the pregranulation mixture of anhydrous perborate, sodium perborate monohydrate, and polymeric fluorocarbon. Where a high degree of initial solution clarity is needed, the PTFE may be present in the amounts from about 0.1% to about 0.2%, and more preferably from about 0.14% to about 0.16% PTFE by weight of the composition.

The monopersulfate compound used in the composition is preferably an alkali metal monopersulfate or an alkaline earth metal monopersulfate. A preferred salt is potassium monopersulfate, especially when present in the form of a triple salt compound with potassium bisulfate and potassium sulfate, e.g. $KHSO_5 \cdot KHSO_4 \cdot K_2SO_4$. This triple potassium salt is available commercially from E. I. duPont DeNemours & Co., Inc. and is sold in the mole ratio 2:1:1 under the trademark "OXONE."

The "OXONE" used in the composition is from about 15% to about 27% by weight of the total composition, preferably from about 18% to about 23%, and most preferably from about 20% to about 21%.

The proteolytic cleaning enzyme for removing proteinaceous material or plaque, and calculus or tartar deposits on dentures is preferably a protease such as "ESPERASE". A number of other known proteases that are particularly active in the pH range of from about 9 to about 10.5 are also acceptable. The enzymes that are active in the range of from about 9.3 to about 9.9 are preferred. The enzymes that are active in the range of from about 9.5 to about 9.7 are most preferred. The enzyme may be present in amounts of about 0.2% to about 5% by weight of the composition. Preferably the enzyme comprises about 0.4% to about 3.8% by weight of the composition. Most preferably the enzyme comprises about 1.7% to about 2.8% by weight of the composition. The enzyme should have an activity of 12 KNPU/gram plus or minus about 20%.

Examples of suitable commercially available proteases include "ALCALASE", "SAVINASE", "ESPERASE" (an alkalophilic variant of *Bacillus licheniformis*), all commercially available from Novo-Nordisk Industries A/S; "MEXATASE" and "MAXACAL" from Gift-Brocades, "KUZUSASE" of Showa Denko; and "BPN" protease from *Bacillus subtilus*, made by Genincor or Sigma. The activity of the proteolytic enzyme included in the composition typically ranges from about 0.1–150 AU/g or its equivalent. Mixtures of different proteolytic enzymes may also be used.

Standard measures of enzyme activity include the Anson Unit (AU), the Kilo Novo Protease Unit (KNPU), and the Glycine Unit (GU). These measures of enzyme activity are well known and defined as follows:

One Anson Unit is the amount of enzyme that digests hemoglobin at an initial rate such that there is liberated per minute an amount of TCA-soluble product which gives the same color with phenol reagent as one milliequivalent of tyrosine. The reaction conditions for this measure are given in NIAS method AF4/5-GB, Modified Anson-Hemoglobin Method for the Determination of Proteolytic Activity.

One Glycine Unit is the amount of enzyme that produces the equivalent of one micromole of glycine per minute under assay conditions.

One Kilo Novo Protease Unit (KNPU) is the amount of enzyme that hydrolyses casein at such a rate that the initial rate of formation of peptide/minute corresponds to I mole of glycine/minute. The standard conditions for carrying out this test are given in NIAS method :AF 162/3-6B Manual DMC (dimethyl casein) Method for the Determination of Proteolytic Activity. The proteolytic enzyme of the invention should have an activity of 12 KNPU/gram plus or minus about 20%.

Sequestering agents are added to the composition to maintain clarity and to promote calculus, or tartar, removal, Preferred sequestering agents include ethylene diamine tetraacetic acid ("EDTA") and its corresponding alkali salts, as well as other polyfunctional organic acids, such as citric acid, maleic acid, fumaric acid and their corresponding salts. The EDTA may be present in amounts of about 1% to 25% by weight of the composition, preferably about 17% to about 23% by weight of the composition, and most preferably about 19% to 21% by weight of the composition.

The EDTA is preferably present as $Na_4EDTA \cdot 2H_2O$, and is preferably dried to a chelating value of 248 or more such that the chelating value is at a sufficient level to compensate for the water which is present in the composition. The EDTA is milled to a U.S.S mesh size profile of:

0% on U.S.S. 20 Mesh

Maximum of 40% on U.S.S. 40 Mesh

Minimum of 75% on U.S.S. 100 Mesh

Maximum of 25% through U.S.S. 100 Mesh

Without intending to be bound by theory, it is believed that the sequestering agent functions in the solution of the invention by reacting with the calcium present in the calculus that accumulates on dentures during the day. This reaction renders underlying proteinaceous material, i.e., plaque, on the dentures susceptible to attack by a proteolytic enzyme also present in the solution. The enzyme in turn attacks this plaque, thereby exposing more calculus to attack by the sequestering agent. Any stain attached to the above deposits are also removed in the process.

This synergistic combination of enzyme and sequestering agent in a powder allows for a more complete removal of both plaque and calculus on dentures. Adsorbed stains, especially those due to accumulated calculus, that had been beyond the reach of single cleansing ingredients are also susceptible to removal by the powder of this invention.

Free halogens, especially chlorine, typically found in tap water and other raw materials, can inactivate proteolytic cleaning enzymes in a system that also includes perborate and monopersulfate. This invention overcomes this problem by using a weight ratio of from about 3:1 to about 1:1, more preferably about 1.7:1, of perborate monohydrate to "OXONE". This ratio reduces the formation of hypochlorite and free chlorine. In a system with this perborate/persulfate ratio, proteolytic cleaning enzymes are not inactivated and are more available for use in synergistic combination with the sequestering agents to remove plaque and calculus deposits, and stained plaque and stained calculus deposits.

Colorants and fragrances may also be used with the composition of this invention. F.D.& C. and D.& C. dyes and lakes and natural colors may be used. The materials acceptable for the foregoing spectrum of use are preferably water soluble, but they may include water insoluble dye materials found in the Kirk-Othmer Encyclopedia of Chemical Technology, Volume #5, pages 857–884, which text is hereby incorporated herein by reference.

The fragrance is preferably spray dried and prepared to a free moisture content of less than about 5.0% and preferably less than about 3.0%.

The fragrances can be any known free flavor or fragrance oil. For example, one fragrance can be selected from the group consisting of thymol, eucalyptol, methyl salicylate, menthol, peppermint oil and spearmint oil.

In addition to the ingredients set forth above, the present compositions may contain a variety of additional ingredients selected on the basis of desired end use. Thus, for example, the compositions may include detergent compounds, such as organic and inorganic detergents, including non-ionic detergents such as the various polyoxyethylene ethers of aromatic and aliphatic alcohols, as well as the polyoxyethylene ethers of hydrophobic propylene oxide polymers. Additionally, ethoxylated acids, and amines are also contemplated. The amount of the detergent is preferably about 0.4% to about 5% by weight, and more preferably about 0.5% to 3% by weight, and most preferably 0.5% to 2.0% by weight of the total cleansing composition. The limiting factor for amounts of detergent is that higher quantities prevent dissolution of the powder and therefore reduce the effective cleaning time. These compounds assist in maintaining a foaming action in the instance where the cleansing Compositions are placed in aqueous solution.

The composition is in the form of a powder, e.g. small granules having particle sizes within the range such as to pass through a 10 or 20 mesh sieve and be retained on, say a 40 mesh sieve (all sieve sizes herein being U.S. Standard). It is preferable that most of the granules have substantially the same overall composition, so that the individual granules will be effervescent. To this end the granules may be produced by thoroughly mixing finely powdered ingredients. Other known techniques for forming granules of substantially uniform composition may be employed.

One preferred embodiment of the invention is a water soluble effervescent denture cleanser composition, which comprises the novel steps of: (a) preparing an anhydrous perborate, perborate monohydrate and polymeric fluorocarbon compound as a first premix; and (b) combining this premix with the other components as described in Examples 1–7, hereinbelow.

When added to water the powders produce a blue colored cleansing bath. This blue color fades after about 3–10 minutes. The rate of fading depends upon the ratio of the persulfate to the perborate, the water bath temperature, and the amount of water used for the bath.

Powders dissolved in water form a cleansing solution that removes plaque, stain and tartar deposits from dentures. The amount of plaque, stain, and tarter deposits removed is dependant upon the amount of time the denture is soaked in the cleansing solution. Rinsing the dentures after soaking will aid in removing the residual denture cleanser solution and additional plaque, stain, and tartar. It is believed that rinsing may also reduce the "slippery" or "slimy" feeling or the "metallic aftertaste" often associated with dentures immediately following the cleaning process with commercial denture cleansers.

A further understanding of the present invention will be gained from the following illustrative examples.

EXAMPLE 1–7

Methods of preparation:

The compositions set forth in Examples 1–7 were prepared as follows. The amounts of each ingredient in the composition are set forth in Table 1.

Example 1 was prepared as follows: A pregranulation mix, or premix, was prepared containing anhydrous sodium perborate, sodium perborate monohydrate, and a small amount of PTFE. The three premix ingredients were combined in a ratio of 14.7/23.9/0.15. All of the anhydrous perborate was used in the premix. The amounts of perborate monohydrate and PTFE in the premix reflect the aforesaid ratio. These three components were blended in a Day blender for about 3 minutes and passed through a chilsonating compacting machine, Model DMC Fitzpatrick, under the following conditions: The chilsonator was set at an air pressure of from about 88 to about 90 psi, and oil pressure of from about 2300 to about 2400 psi, and the roller at high speed using 2–3 amps. The compacted material was then passed through a Model 197S comil having a 0.175 inch spacer, with a 0.032 inch screen at 4200 RPM. The compacted anhydrous perborate, perborate monohydrate and PTFE, hereinafter known as the premix, typically had a U.S.S. Mesh distribution of:

14% on a size 40 mesh screen,

22% on a size 60 mesh screen,

15% on a size 80 mesh screen,

16% on a size 100 mesh screen,

33% through a 100 mesh screen.

The premix had an untapped density of 0.58 grams/ml and a tapped density (100 taps) of 0.79 grams/ml.

The premix as prepared is used in the formulation at approximately 7% by weight.

In a suitable Day blender container set at 50 RPM the following ingredients were combined in sequence in evenly spaced intervals to achieve the powder composition of the present invention: sodium bicarbonate; dyes and water; sodium tripolyphosphate; sodium carbonate; citric acid; EDTA; "OXONE"; the remainder of the unpregranulated sodium perborate monohydrate; the premix; flavor preblend; sodium saccharin; spray dried fragrance; sodium sulfate; lathanol; sodium benzoate.

For examples 2–7, a premix was prepared containing anhydrous sodium perborate, sodium perborate monohydrate, and PTFE in the ratio of 45.26/54.18/0.56. All of the anhydrous perborate was used in the premix. The amounts of perborate monohydrate and PTFE in the premix reflect the aforesaid ratio. These three components were blended in a Day blender for about 3 minutes and passed through a chilsonating compacting machine, Model DMC Fitzpatrick, under the following conditions: The chilsonator was set at an air pressure of 89 psi, the oil pressure: was set at 2350 psi and the roller at high speed using 2–3 amps. The compacted material was then passed through a Model 1972 comil having 0.175 inch spacer, with a 0.032 inch screen at 4200 RPM. The compacted anhydrous perborate, perborate monohydrate and PTFE, hereinafter known as the premix, typically had a U.S. S. Mesh size distribution of:

14% on a size 40 mesh screen,

25% on a size 60 mesh screen,

11% on a size 80 mesh screen,

15% on a size 100 mesh screen,

35% through a 100 mesh screen.

The premix had an untapped density of 0.58 grams/ml and a tapped density (100 taps) of 0.76 grams/ml.

For best results, the moisture content of the sodium perborate monohydrate should be less than 1.0%. The premix as prepared is used in the formulation at approximately 25% by weight.

After the premix was prepared, the preparation of Examples 2, 5, 6, and 7 was completed as follows: In a suitable Day Blender set at 50 RPM the following ingredients were added in sequence at approximately 90-second intervals; the remainder of the non-pregranulated sodium perborate monohydrate that was not used to prepare the premix; EDTA; potassium monopersulfate; the premix; sodium tripolyphosphate; a preblend of the dyes and sodium bicarbonate and sodium sulfate; solid fragrance; liquid fragrance; and "ESPERASE". The mixture was mixed until the materials were evenly dispersed up to a maximum of 26 minutes. Detergent was then added to the mixture and the mixture was mixed up to a maximum of 3 additional minutes. Total maximum mixing time was 29 minutes. The total mixing time of 29 minutes is not critical.

The preparation of Examples 3 and 4 was completed in the same manner as Examples 2, 5, 6, and 7, except that EDTA was not added in Example 3, and "ESPERASE" was not added in Example 4. (See Table 1).

The compositions of the compositions prepared according to Examples 1–7 are set forth in Table 1.

TABLE 1

| Example | Composition Composition | | | | | | |
|---|---|---|---|---|---|---|---|
|  | 1 | 2 | 3 | 4 | 5 | 6 | 7 |
| Sodium Perborate Monohydrate | 387 | 908.0 | 908.0 | 908.0 | 908.0 | 554.4 | 908.0 |
| Sodium Perborate Anhydrous | 83.0 | 365.0 | 365.0 | 365.0 | 365.0 | 223.1 | 365.0 |
| $Na_4EDTA.2H_2O$ | 119.0 | 540.0 | — | 540.0 | 540.0 | 329.4 | 540.0 |
| "OXONE" (Potassium Mono Persulfate) | 1221.0 | 552.0 | 552.0 | 552.0 | 552.0 | 336.7 | 552.0 |
| Sodium Saccharin | 7.0 | 7.0 | 7.0 | 7.0 | 7.0 | 7.0 | 7.0 |
| "LATHONOL" | 20.0 | 17.2 | 17.2 | 17.2 | 17.2 | 17.2 | 17.2 |
| PTFE | 3.0 | 3.8 | 3.8 | 3.8 | 3.8 | 2.3 | 3.8 |
| "ESPERASE" 12knpu/gm | — | 40.0 | 40.0 | — | 40.0 | 24.4 | 44.0 |
| Fragrance (Spray Dried) Spearmint Type | 30.0 | 45.0 | 45.0 | 45.0 | 30.0 | 45.0 | — |
| Mixed Fragrances (Spray Dried) (Listerine Essential Oils) | — | — | — | — | — | — | 45.0 |
| Fragrance (Liquid) (Spearmint) | — | — | — | — | 5.4 | — | — |
| Color | 5.1 | 5.05 | 5.05 | 5.05 | 5.05 | 3.1 | 5.05 |
| Sodium Tripoly-Phosphate | 318.0 | 74.3 | 74.3 | 74.3 | 74.3 | 45.2 | 74.3 |
| $Na_2CO_3$ | 285.0 | — | — | — | — | — | — |
| Sodium Sulfate | 150.0 | 67.5 | 67.5 | 67.5 | 67.5 | 41.2 | 67.5 |
| Citric Acid | 119.0 | — | — | — | — | — | — |
| $NaHCO_3$ | 342.0 | 25.0 | 25.0 | 25.0 | 25.0 | 15.3 | 25.0 |
| Sodium Benzoate | 20.0 | — | — | — | — | — | — |
| water | 10.0 | — | — | — | — | — | — |
| Total Weight (grams per 1000 compositions) | 3129.0 | 2649.9 | 2109.9 | 2609.9 | 2640.3 | 1638.3 | 2649.9 |

Example 1 is a comparative prior art example of a known composition showing a composition having a higher weight percent of monopersulfate and a lower perborate monohydrate weight percent compared to the inventive compositions.

Example 2, 5, 6 and 7 comprise examples of the invention. Example 2 has both cleaning enzymes and high levels of EDTA. Example 5 is the inventive composition with reduced spray dried fragrance and added liquid fragrance. Example 6 is a reduced weight formulation of Example 2 with the same levels of detergent and fragrance. Example 7 is the inventive formulation composition wherein the spray dried fragrances used are the essential oils used in LISTERINE® antiseptic mouth rinse in the ratio of 1.00/1.50/2.17/1.41 for menthol, thymol, eucalyptol and methyl salicylate respectively at a 20% load based on weight. Example 3 is the same formulation as Example 2 without Na4EDTA.2H$_2$0. Example 4 is the same formulation as Example 2 without "ESPERASE".

The purpose of the above Examples is to illustrate some embodiments of the present invention without implying limitations. It will be apparent to those skilled in the art that various modifications and variations may be made in the apparatus or procedure of the invention without departing from the scope or spirit of the invention.

We claim:

1. A denture cleansing composition in powder form derived from a mixture comprising:
   (a) a pregranulated compressed mixture of an anhydrous perborate in an amount of from about 5% to about 25% by weight of said composition, a perborate monohydrate and a lubricant and compression aid, wherein the weight ratio of anhydrous perborate to said perborate monohydrate in said pregranulated mixture is from about 1:3 to about 1:1 the amount of perborate monhydrate in the premixture being reflected by the ratio; and
   (b) a monopersulfate compound in an amount of from about 15% to about 27% by weight of said composition;
   (c) a non-granulated perborate monohydrate wherein the total amount of granulated and non-granulated perborate monhydrate is in an amount of from about 30% to about 45% by weight of said denture cleansing composition;
   (d) an effective amount of one or more proteolytic enzymes to disrupt the proteinaceous material in plaque; and
   (e) an effective amount of a sequestering agent to remove calcium deposits and calculus deposits.

2. The denture cleansing composition of claim 1 wherein;
   (i) said anhydrous perborate is potassium or sodium anhydrous perborate;
   (ii) said lubricant and compression aid is in an amount of from about 0.1% to about 0.8% by weight of said pregranulated compressed mixture, and wherein said lubricant and compression aid is polytetrafluorethylene;
   (iii) said monopersulfate compound is a triple potassium salt with the formula KHSO$_5$.KHSO$_4$.K$_2$SO$_4$ and a mole ratio of 2:1:1.;
   (iv) said proteolytic enzyme is in an amount of from about 0.2% to about 5% by weight of said composition, and wherein said proteolytic enzyme is protease derived from a variant of *Bacillus licheniformis*; and
   (v) said sequestering agent is in an amount of from about 1% to about 25% by weight of said composition, and wherein said sequestering agent is Na$_4$EDTA.2H$_2$O.

3. The composition of claim 1, wherein said anhydrous perborate comprises about 13% to about 14% by weight of said composition.

4. The composition of claim 1, wherein said perborate monohydrate comprises from about 33% to about 35% by weight of the total cleansing composition.

5. The composition of claim 1 wherein said lubricant and compression aid is polytetrafluourethylene.

6. The composition of claim 1, wherein said lubricant and compression aid comprises from about 0.14% to about 0.16% by weight of the pregranulated compressed mixture.

7. The composition of claim 1 wherein said monopersulfate compound is a triple potassium salt with the formula KHSO$_5$. KHSO$_4$.K$_2$SO$_4$ and a mole ratio of 2:1:1.

8. The composition of claim 7, wherein said monopersulfate compound comprises from about 15% to about 27% by weight of said composition.

9. The composition of claim 1, wherein said sequestering agent is EDTA.

10. The composition of claim 9, wherein said EDTA is Na$_4$EDTA.2H$_2$O.

11. The composition of claim 10, wherein said Na$_4$EDTA.2H$_2$O comprises from about 1% to about 25% by weight of said composition.

12. The composition of claim 11 wherein the mesh-size profile of said EDTA is a maximum of 25% through U.S.S. 100 mesh screen and 0% remaining on U.S.S. 20 mesh screen.

13. The composition of claim 10, wherein the chelating value of said Na$_4$EDTA.$_2$H$_2$O is at least about 238.

14. The composition of claim 1 wherein said proteolytic enzyme is a protease derived from *Bacillus lichenformis*.

15. The composition of claim 1 wherein said proteolytic enzymes are present in an amount from about 0.2% to about 5% by weight of said composition.

16. The composition of claim 1, wherein said monopersulfate is selected from the group consisting of alkali metal monopersulfates and alkaline earth metal monopersulfates.

17. The composition of claim 1, wherein said monopersulfate is sodium or potassium monopersulfate.

18. The composition of claim 1, wherein said anhydrous perborate is selected from the group consisting of alkali metal perborates and alkaline earth metal perborates.

19. The composition of claim 1, wherein said anhydrous perborate is potassium or sodium anhydrous perborate.

20. The composition of claim 1, wherein the weight ratio of perborate monohydrate to anhydrous perborate to polymeric fluorocarbon compound is about 54.2:45.2:0.6.

21. The composition of claim 1, wherein said perborate monohydrate is potassium or sodium perborate monohydrate.

22. The composition of claim 1, wherein the weight ratio of perborate monohydrate/monopersulfate compound is from about 3:1 to about 1:1.

23. The composition of claim 22, wherein the weight ratio of perborate monohydrate/monopersulfate compound is about 1.7:1.

24. The composition of claim 1, wherein a detergent is a component of said composition.

25. The composition of claim 24, wherein said detergent is an anionic detergent.

26. The composition of claim 25, wherein said anionic detergent is present in the amount of up to about 5% by weight of the composition.

27. A process for preparing an effervescent denture cleansing powder according to claim 1 comprising the steps of:

(a) preparing a compacted compressed mixture comprising anhydrous perborate salts and perborate monohydrate salts in combination with a lubricant and compression aid; and (b) grinding said compacted mixture into a pregranulation mixture, or premix; and (c) adding the pregranulation mixture, or premix, to the other materials in the denture cleansing composition and mixing; and (d) adding detergent to the mixture and mixing for up to 3 minutes.

28. A denture cleansing composition in powder form derived from a mixture comprising:

(a) a pregranulated compressed mixture of an anhydrous perborate in an amount of from about 5% to about 25% by weight of said composition, a perborate monohydrate, and a lubricant and compression aid, wherein the weight ratio of anhydrous perborate to said perborate monohydrate in said pregranulated mixture is from about 1:3 to about 1:1, the amount of perborate monohydrate in the premixture being reflected by the ratio;

(b) a monopersulfate compound in an amount of from about 15% to about 27% by weight of said composition;

(c) non-granulated perborate monohydrate wherein the total amount of granulated and non-granulated perborate monohydrate is in an mount of from about 30% to about 60% by weight of said denture cleansing composition;

(d) an effective amount of a sequestering agent to remove calcium deposits and calculus deposits; and (e) an effective amount of at least one fragrance.

29. The composition of claim 28 wherein the fragrance is thymol.

30. The composition of claim 28 wherein the fragrance is eucalyptol.

31. The composition of claim 28 wherein the fragrance is methyl salicylate.

32. The composition of claim 28 wherein the fragrance is menthol.

33. A process for preparing a denture cleansing powder according to claim 28 comprising the steps of:

(a) preparing a compacted compressed mixture comprising anhydrous perborate salts and perborate monohydrate salts in combination with a lubricant and compression aid;

(b) grinding said compacted mixture into a pregranulation mixture, or premix;

(c) adding the pregranulation mixture, or premix, to the other materials in the denture cleansing composition and mixing;

(d) adding detergent to the mixture and mixing; and (e) adding at least one fragrance to the mixture.

34. The process for claim 33 wherein the fragrance is selected from the group consisting of thymol, eucalyptol, methyl salicylate and menthol.

* * * * *